United States Patent
Lee et al.

(10) Patent No.: US 9,018,379 B1
(45) Date of Patent: Apr. 28, 2015

(54) PROCESS OF PREPARING SOLIFENACIN OR SALT THEREOF, AND NOVEL INTERMEDIATE USED IN THE PROCESS

(71) Applicant: Kyung Dong Pharm. Co., Ltd., Gyeonggi-do (KR)

(72) Inventors: Byoung Suk Lee, Seoul (KR); Sang Hoon Shin, Gyeonggi-do (KR); Ki Young Lee, Gyeonggi-do (KR)

(73) Assignee: Kyung Dong Pharm. Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/382,529

(22) PCT Filed: Mar. 21, 2013

(86) PCT No.: PCT/KR2013/002358
§ 371 (c)(1),
(2) Date: Sep. 2, 2014

(87) PCT Pub. No.: WO2013/147458
PCT Pub. Date: Oct. 3, 2013

(30) Foreign Application Priority Data

Mar. 28, 2012 (KR) .................. 10-2012-0031492

(51) Int. Cl.
*C07D 453/02* (2006.01)
(52) U.S. Cl.
CPC .................................. *C07D 453/02* (2013.01)
(58) Field of Classification Search
CPC .................................................. C07D 453/02
USPC ......................................................... 546/137
See application file for complete search history.

(56) References Cited

U.S. PATENT DOCUMENTS

| | | | | |
|---|---|---|---|---|
| 6,017,927 | A | 1/2000 | Takeuchi et al. | 514/305 |
| 6,680,386 | B2 | 1/2004 | Lee et al. | 546/157 |
| 7,741,489 | B2 | 6/2010 | Puig Serrano et al. | 546/137 |
| 7,829,715 | B2 | 11/2010 | Inakoshi et al. | 546/134 |
| 2007/0173528 | A1 | 7/2007 | Perlman et al. | 514/305 |
| 2007/0185329 | A1 | 8/2007 | Inakoshi et al. | 546/137 |
| 2008/0242697 | A1 | 10/2008 | Puig Serrano et al. | 514/305 |
| 2008/0287680 | A1 | 11/2008 | Ishii et al. | 546/134 |
| 2009/0099365 | A1 | 4/2009 | Perlman et al. | 546/134 |

FOREIGN PATENT DOCUMENTS

| | | |
|---|---|---|
| JP | 2008-535931 | 9/2008 |
| JP | 2009-538362 | 11/2009 |
| KR | 10-2010-0016116 | 2/2010 |
| WO | WO 2005/075474 | 8/2005 |
| WO | WO 2005/105795 | 11/2005 |
| WO | WO 2008/062282 | 5/2008 |

OTHER PUBLICATIONS

Letter/Written Disclosure of the Information Disclosure Statement for the above-referenced application, mailed on Dec. 10, 2014, 2 pages.
International Search Report and Written Opinion, issued Jul. 29, 2013, in connection with International Patent Application No. PCT/KR2013/002358, 7 pages.
International Preliminary Report on Patentability, issued Oct. 1, 2014, in connection with International Patent Application No. PCT/KR2013/002358, 5 pages.

*Primary Examiner* — Niloofar Rahmani
(74) *Attorney, Agent, or Firm* — McKenna Long & Aldridge LLP; Stephanie Seidman; Frank J. Miskiel

(57) ABSTRACT

Disclosed herein is a method of preparing solifenacin or a salt thereof, including the steps of: (a) reacting (R)-quinuclidinol with bis(pentafluorophenyl)carbonate in an organic solvent to prepare a solifenacin intermediate, (3R)-1-azabicyclo[2,2,2]oct-3-yl pentafluorophenylcarbonate, and (b) reacting the solifenacin intermediate with (1S)-1-phenyl-1,2,3,4-tetrahydroisoquinoline in an organic solvent to prepare solifenacin. The method is advantageous in that high-purity solifenacin or a salt thereof can be simply and efficiently prepared with high yield using a novel intermediate.

12 Claims, No Drawings

PROCESS OF PREPARING SOLIFENACIN OR SALT THEREOF, AND NOVEL INTERMEDIATE USED IN THE PROCESS

RELATED APPLICATIONS

This application is the National Stage of International Application. No. PCT/KR2013/002358, filed 21 Mar. 2013, which claims benefit of priority to Korean Patent Application No. 10-2012-0031492, filed 28 Mar. 2012, the specification of which is incorporated by reference herein.

TECHNICAL FIELD

The present invention relates to a method of preparing solifenacin or a salt thereof. More particularly, the present invention relates to a method of preparing a novel solifenacin intermediate and a method of preparing solifenacin or a salt thereof using the intermediate.

BACKGROUND ART

Solifenacin succinate ((1S)-(3R)-1-azabicyclo[2,2,2]oct-3-yl-3,4-dihydro-1-phenyl-2(1H)-isoquinoline carboxylate succinate), represented by Formula (I) below, is a competitive and selective M3 muscarine receptor antagonist, and is known as a compound used to treat overactive bladder symptoms such as urgent urinary incontinence, urinary urgency, urinary frequency and the like.

[Formula I]

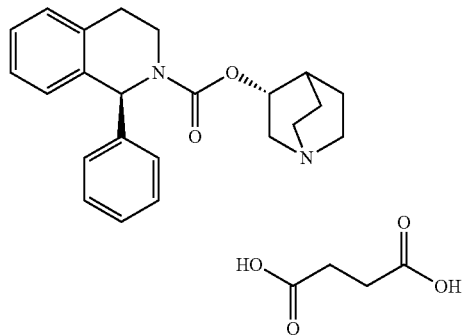

Conventional methods of preparing solifenacin or solifenacin succinate are disclosed in U.S. Pat. No. 6,017,927, International Patent Publication No. 2005/075474 (WO 2005/075474) and International Patent Publication No. 2005/105795 (WO 2005/105795).

U.S. Pat. No. 6,017,927 discloses two synthesis pathways for preparing solifenacin, synthesis pathway A and synthesis pathway B represented by Reaction Formula 1 below.

[Reaction Formula 1]

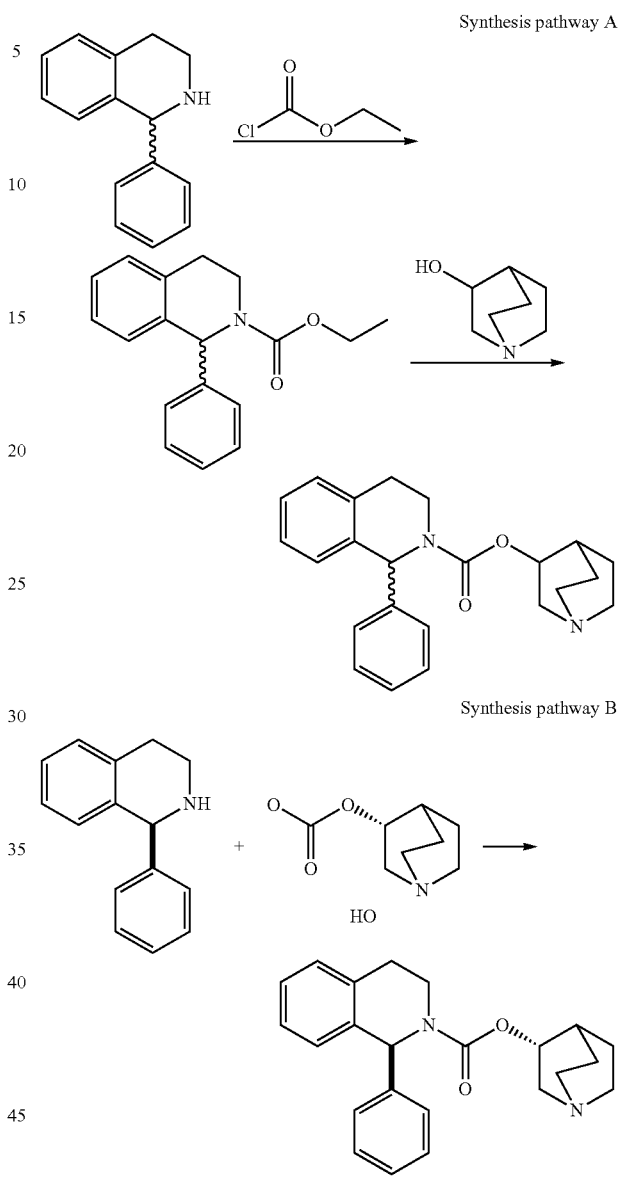

In the synthesis pathway A, the transesterification reaction of a racemic mixture of 1-phenyl-1,2,3,4-tetrahydroisoquinoline ethyl ester and quinuclidinol was conducted in a toluene suspension under the presence of sodium hydride (NaH), and the obtained mixture was refluxed and stirred. In this case, the obtained diastereomeric mixture was optically separated by high performance liquid chromatography (HPLC).

In the synthesis pathway B, quinuclidinyl chloroformate mono-hydrochloride was reacted with (1S)-1-phenyl-1,2,3, 4-tetrahydroisoquinoline in the presence of sodium hydride (NaH) to synthesize solifenacin.

However, the method of preparing solifenacin using the synthesis pathway A and synthesis pathway B is problematic in that it requires high cost, its efficiency is not high due to post-treatment processes, and it is not suitable for producing solifenacin on an industrial scale.

Moreover, ethyl carboxylate used in the synthesis pathway A produces ethanol as a by-product of a transesterification reaction. In this case, since ethanol initiates a nucleophilic attack against solifenacin in the presence of a base, in order to continue the reaction, there is a problem in that ethanol must be separated from a reaction system using an azeotrope with toluene or a method related thereto, which is very industrially difficult. Further, the synthesis pathway A is also problematic in that it is difficult to obtain solifenacin having high optical purity because solifenacin is racemized.

Further, in the synthesis pathway A and the synthesis pathway B, the mixture was heated under reflux in order to accelerate the reaction in the solifenacin synthesis process, and a very strong base, such as sodium hydride (NaH), was used. Therefore, there are problems in that it is not easy to control the reaction and it is difficult to produce solifenacin on an industrial scale.

International Patent Publication No. 2005/075474 (WO 2005/075474) discloses another synthesis pathway for preparing solifenacin and solifenacin succinate, as represented by Reaction Formula 2 below.

paring solifenacin, as represented by Reaction Formula 3 below.

[Reaction Formula 3]

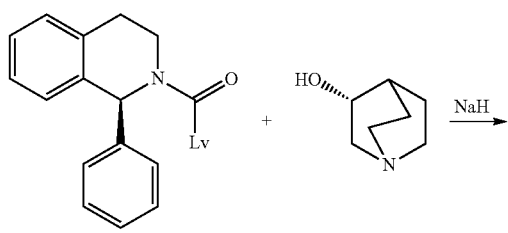

[Reaction Formula 2]

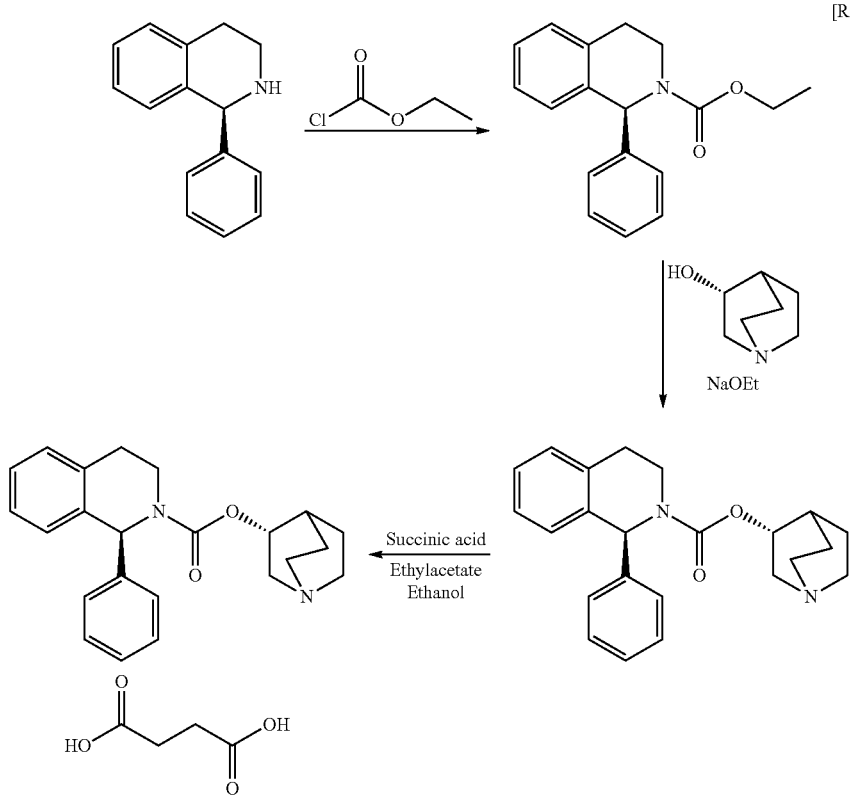

However, as mentioned in U.S. Pat. No. 6,017,927, this synthesis pathway of Reaction Formula 2 is also problematic in that a reaction is performed using ethylchloroformate in the presence of a base, and thus ethanol is produced in the second step of the reaction as a by-product.

International Patent Publication No. 2005/105795 (WO 2005/105795) discloses another synthesis pathway for pre- -continued

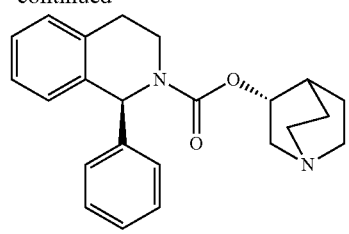

As shown in Reaction Formula 3 above, solifenacin is prepared through an intermediate, which is formed from (1S)-1-phenyl-1,2,3,4-tetrahydroisoquinoline with a leaving group(Lv) such as 1H-imidazole-1-yl, 2,5-dioxopyrrolidine-1-yloxy, 3-methyl-1H-imidazol-3-lium-1-yl or chloride and then conducted a condensation reaction with (R)-quinuclidinol in a mixed solvent of toluene and dimethylsulfoxide or in a single solvent of toluene by refluxing and stirring in the presence of sodium hydride (NaH).

However, this synthesis pathway of Reaction Formula 3 is also problematic in that it is not easy to control a reaction process because a strong base such as sodium hydride (NaH) is used, a purification process using chromatography is required and a moisture-sensitive leaving group is used.

Accordingly, in order to solve the above-mentioned problems, the present inventors have devised a high yield method of preparing solifenacin or a salt thereof, in which high-purity solifenacin or a salt thereof can be simply and efficiently prepared at room temperature without using a base, and which can be industrially used.

DISCLOSURE OF INVENTION

Technical Problem

An object of the present invention is to provide a method of preparing high-purity solifenacin or a salt thereof with high yield.

Another object of the present invention is to provide a method of preparing solifenacin or a salt thereof in large amounts by a simple process.

Still another object of the present invention is to provide a novel intermediate used in the method and a method of preparing the novel intermediate.

Solution to Problem

In order to accomplish the above objects, an aspect of the present invention provides a method of preparing solifenacin or a salt thereof, comprising the steps of: (a) reacting (R)-quinuclidinol of Formula (VI) below with bis(pentafluorophenyl)carbonate of Formula (VII) below in an organic solvent to prepare (3R)-1-azabicyclo[2,2,2]oct-3-yl pentafluorophenylcarbonate of Formula (IV) below; and (b) reacting the (3R)-1-azabicyclo[2,2,2]oct-3-ylpentafluorophenylcarbonate of Formula (IV) below with (1S)-1-phenyl-1,2,3,4-tetrahydroisoquinoline of Formula (V) below in an organic solvent to prepare solifenacin of Formula (II) below:

[Formula II]

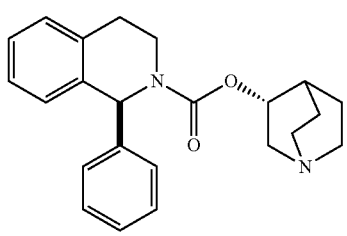

(II)

[Formula IV]

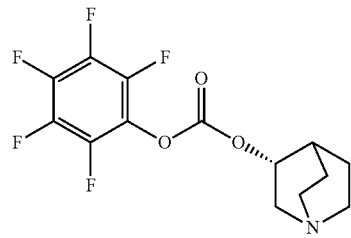

(IV)

[Formula V]

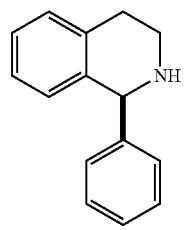

(V)

[Formula VI]

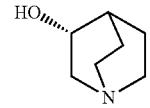

(VI)

[Formula VII]

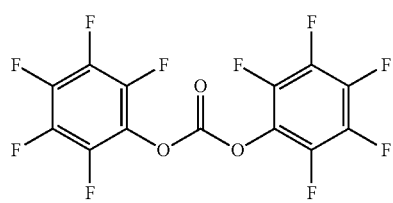

(VII)

Another aspect of the present invention provides a compound represented by Formula (IV) below, which is used as an intermediate for preparing solifenacin:

[Formula IV]

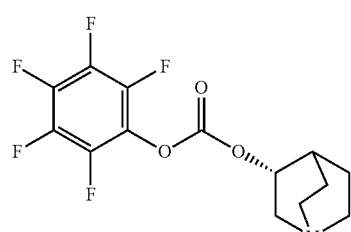

(IV)

Still another aspect of the present invention provides a method of preparing a compound of Formula (IV) below, comprising the step of reacting (R)-quinuclidinol of Formula (VI) below with bis(pentafluorophenyl)carbonate of Formula (VII) below in an organic solvent.

[Formula IV]

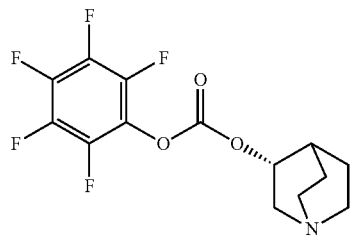
(IV)

[Formula VI]

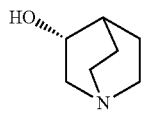
(VI)

[Formula VII]

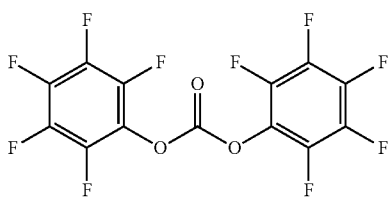
(VII)

Advantageous Effects of Invention

[51] The present invention can provide a method of preparing high purity solifenacin or a salt thereof with high yield.

Further, the present invention can provide a method of preparing solifenacin or a salt thereof that can produce large amounts by a simple process.

Further, the present invention can provide a novel intermediate and a method of preparing the novel intermediate used in the process.

BEST MODE FOR CARRYING OUT THE INVENTION

Method of Preparing Solifenacin or a Salt Thereof

The present invention provides a novel synthesis pathway for preparing solifenacin or a salt thereof, represented by Reaction Formula 4 below:

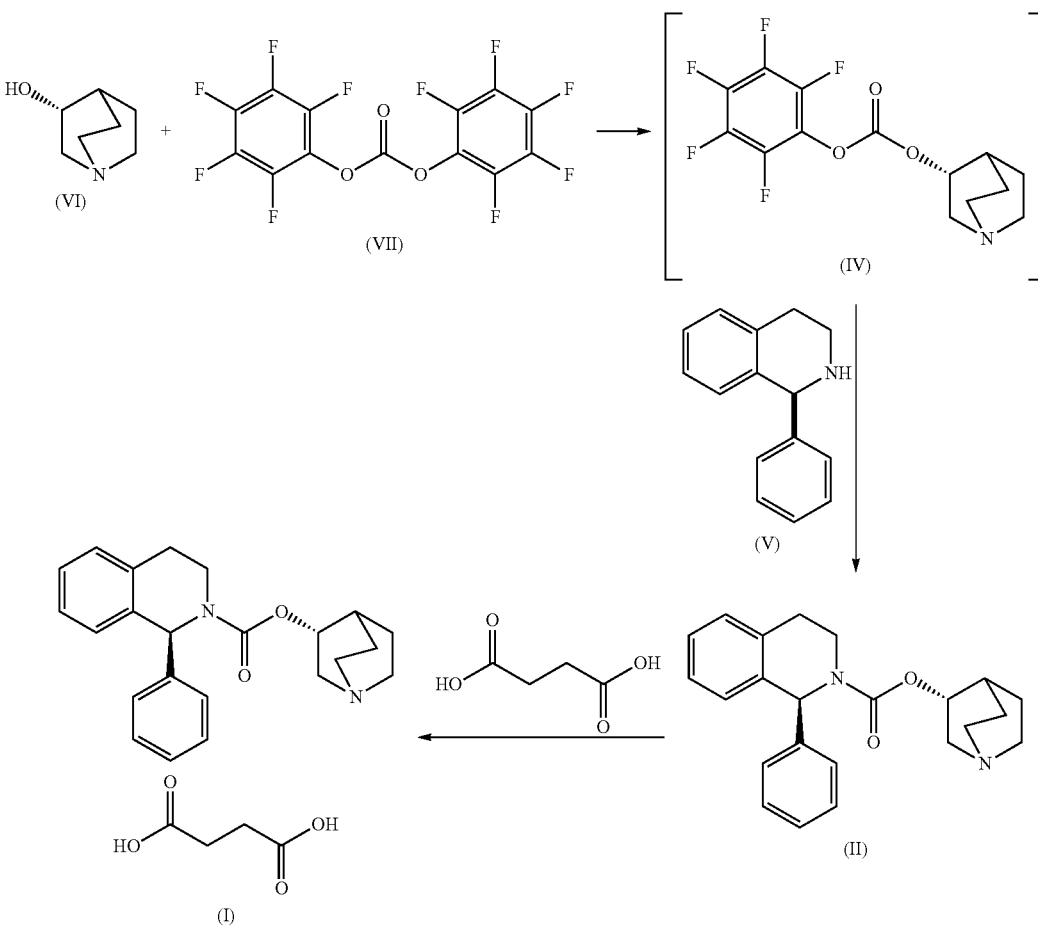

As shown in Reaction Formula 4, the method of preparing solifenacin or a salt thereof according to the present invention includes the steps of: (a) preparing a solifenacin intermediate; (b) preparing solifenacin using the intermediate; and (c) converting the solifenacin into a solifenacin salt.

Hereinafter, the method of preparing solifenacin or a salt thereof according to the present invention will be described in detail with respect to each step.

Step (a): Preparation of Solifenacin Intermediate

The present invention provides a method of preparing (3R)-1-azabicyclo[2,2,2]oct-3-ylpentafluorophenylcarbonate of Formula (IV) below, which can be used as an intermediate for preparing solifenacin or a salt thereof:

[Formula IV]

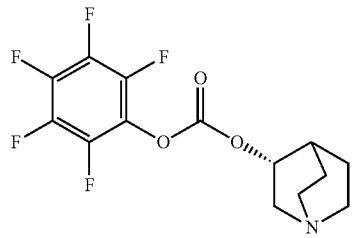

(IV)

The solifenacin intermediate is prepared by reacting (R)-quinuclidinol of Formula (VI) below with bis(pentafluorophenyl)carbonate of Formula (VII) below in an organic solvent, as shown in Reaction Formula 5 below:

[Formula VI]

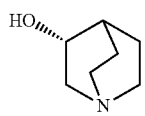

(VI)

[Formula VII]

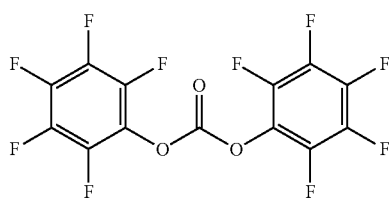

(VII)

[Reaction Formula 5]

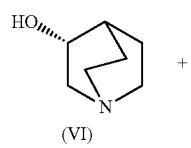

(VI)

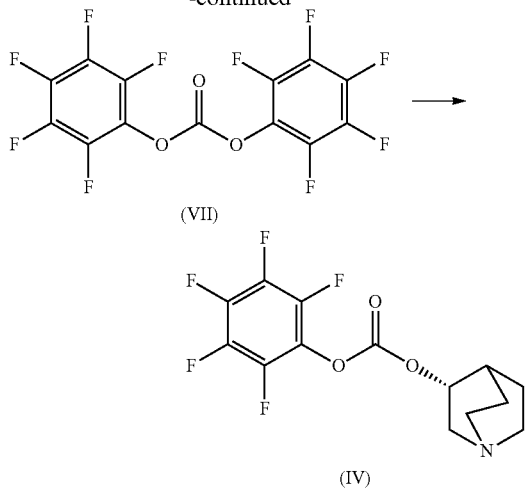

(VII)

(IV)

The bis(pentafluorophenyl)carbonate of Formula (VII) can be used at an amount of 1 to 3 molar equivalent per 1 molar equivalent of (R)-quinuclidinol of Formula (VI), preferably 1 to 1.5 molar equivalent.

The organic solvent can be selected from the group including of toluene, ethyl acetate, dichloromethane, acetone, isopropanol and mixtures thereof. The organic solvent can be used at an amount of 2 mL to 20 mL per 1 g of (R)-quinuclidinol of Formula (VI), and preferably 5 ml to 15 mL.

The reaction of Reaction Formula 5 above may be performed at −40° C. to 100° C., and preferably 10° C. to 30° C. Particularly, the reaction of Reaction Formula 5 may be performed at room temperature, and thus this reaction can be performed under moderate conditions without conducting an additional process such as heating, cooling or the like.

It is preferred that the reaction of Reaction Formula 5 be performed for 2 hours to 12 hours at the mentioned temperature.

Further, the reaction of Reaction Formula 5 may be performed without using any base or catalyst even under the moderate conditions.

Further, according to the reaction of Reaction Formula 5, the solifenacin intermediate of Formula (IV) can be obtained with high yield of more than 87% under the moderate reaction conditions.

Step (b): Preparation of Solifenacin

The present invention provides a method of preparing solifenacine by reacting the solifenacin intermediate of Formula (IV) prepared in the step (a) with (1S)-1-phenyl-1,2,3,4-tetrahydroisoquinoline of Formula (V) below in an organic solvent, as shown in Reaction Formula 6 below:

[Formula V]

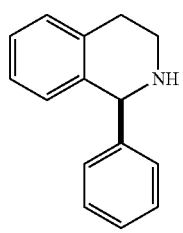

(V)

[Reaction Formula 6]

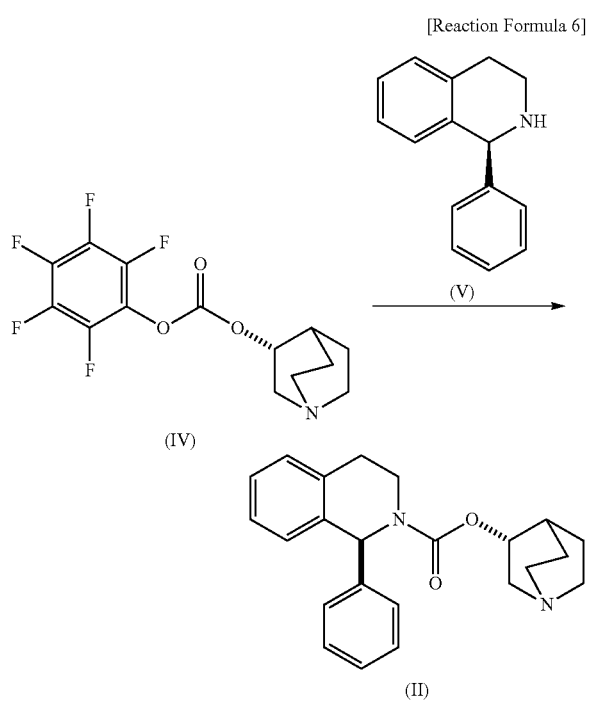

extracted with toluene, and then the extracted solution is concentrated, thereby obtain oily solifenacin.

Further, according to the reaction of Reaction Formula 6, the solifenacin of Formula (II) can be obtained with high yield of more than 87% under the moderate reaction conditions.

Step (c): Preparation of a Salt of Solifenacin

The present invention provides a method of converting the solifenacin of Formula (II) prepared in the step (b) into a salt thereof.

The salt of solifenacin may be an acid addition salt prepared by reacting the solifenacin of Formula (II) prepared in the step (b) with an inorganic or organic acid in an organic solvent.

The inorganic acid may be hydrochloric acid, hydrobromic acid, hydroiodic acid, sulfuric acid, nitric acid, phosphoric acid or the like. The organic acid may be formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid or the like. Preferably, the organic acid may be succinic acid.

The pathway of preparing solifenacin succinate of Formula (I), which is an acid addition salt of solefenacin, is represented by Reaction Formula 7 below:

[Reaction Formula 7]

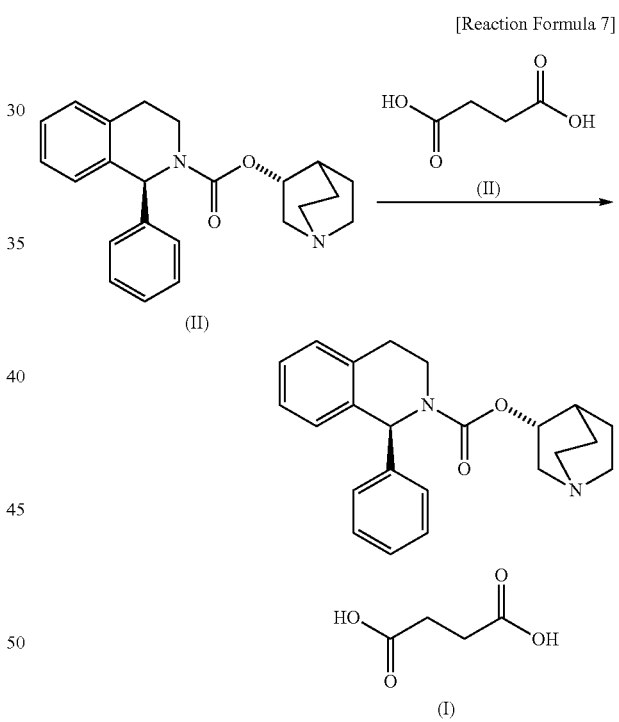

The reaction of Reaction Formula 6 above may be performed by an in-situ reaction in which the (1S)-1-phenyl-1,2,3,4-tetrahydroisoquinoline of Formula (V) is added dropwise without dissociating the (3R)-1-azabicyclo[2,2,2]oct-3-yl pentafluorophenylcarbonate of Formula (IV) prepared in the step (a).

The (1S)-1-phenyl-1,2,3,4-tetrahydroisoquinoline of Formula (V) can be used at an amount of 1 to 3 molar equivalent per 1 molar equivalent of (3R)-1-azabicyclo[2,2,2]oct-3-yl-pentafluorophenylcarbonate of Formula (IV), preferably 1 to 1.5 molar equivalent.

The organic solvent, just like in the step (a), may be selected from the group including of toluene, ethyl acetate, dichloromethane, acetone, isopropanol and mixtures thereof. Further, the organic solvent in the step (b) may be same with that of in the step (a).

The reaction of Reaction Formula 6 above may be performed at −40° C. to 100° C., and preferably, 10° C. to 30° C. Particularly, the reaction of Reaction Formula 6 may be performed at room temperature, and thus this reaction can be performed under moderate conditions without conducting an additional process such as heating, cooling or the like.

It is preferred that the reaction of Reaction Formula 6 be performed for 2 hours to 12 hours at the mentioned temperature.

Further, the reaction of Reaction Formula 6 may be performed without using any base or catalyst even under the moderate conditions.

After the reaction of Reaction Formula 6 is completed, the solifenacin of Formula (II) can be obtained by the following purification process. Specifically, water is added to the solution obtained after the completion of the reaction of Reaction Formula 6, a strong acid such as hydrochloric acid is added dropwise into the solution to adjust the pH of the solution to 1~2, an organic layer is separated from the solution to remove pentafluorophenol produced during the reaction, a base such as ammonium hydroxide is further dripped into the solution to adjust the pH of the solution to 9~10, the solution is Examples of the organic solvent used in the reaction of Reaction Formula 7 may include: aliphatic alcohols, such as ethanol, 1-butanol, isopropanol and the like; ketones, such as acetone, methyl isobutyl ketone, and the like; esters, such as ethyl acetate, n-butyl acetate, ethyl propionate, and the like; aromatic hydrocarbons, such as tolune and the like; and polar aliphatic hydrocarbons, such as n-hexane, heptane, and the like. Preferably, acetone, toluene or a mixture thereof may be used as the organic solvent.

The reaction of Reaction Formula 7 may be performed by stirring the reaction mixture at 50° C.~65° C. for 20 minutes~1 hour and then further stirring the reaction mixture at 10° C.~15° C. for 1 hour~3 hours.

When the reaction is completed, the prepared solifenacin is filtered, washed and then dried to obtain solifenacin succinate.

The solifenacin succinate obtained in this way may be crystalline solifenacin succinate, and this crystalline solifenacin succinate has a melting point of 146° C.~148° C.

Further, according to the reaction of Reaction Formula 7, the solifenacin succinate of Formula (I) can be obtained with high yield of more than 78%.

Novel Solifenacin Intermediate and Preparation Method Thereof

The present invention provides a novel intermediate represented by Formula (IV) below, which can be used to prepare solifenacin and a salt thereof, and a method of preparing the intermediate:

[Formula IV]

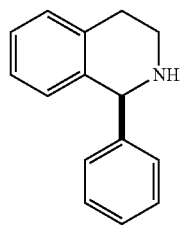

(V)

The method of preparing a solifenacin intermediate is the same as the step (a) of the method of preparing solifenacin or a salt thereof.

The solifenacin intermediate is a material which can be simply and efficiently prepared at room temperature without using a base by the step (a). Further, the solifenacin intermediate is used as a reactant in the step (b), and can be easily converted into solifenacin at room temperature without using a base.

The method of preparing solifenacin or a salt thereof using a solifenacin intermediate is advantageous in that high-purity solifenacin or a salt thereof can be prepared with high yield by a simple process.

Therefore, the solifenacin intermediate of Formula (IV) can be used to produce solifenacin or a salt thereof in large amounts.

Mode for the Invention

Hereinafter, the present invention will be described in detail with reference to the following Examples. These Examples are set forth to illustrate the present invention, and the scope of the present invention is not limited thereto.

Example 1

Preparation of Solifenacin Intermediate 127.2 g (1.0 mol) of (R)-quinuclidinol was dissolved in 1270 mL of toluene and then stirred at 10~15° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 10~15° C. for 7~8 hours. After confirming the completion of a reaction using thin layer chromatography (TLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, 1270 mL of water was added to the reaction solution, and then the pH of the reaction solution was adjusted to 9~10 using ammonium hydroxide. Then, an organic layer was separated from the reaction solution. Finally, the reaction solution was washed with 1270 mL of water, dried with $MgSO_4$ and then concentrated under reduced pressure to obtain 304.9 g (90.4%) of (3R)-1-azabicyclo[2,2,2]oct-3-yl pentafluorophenylcarbonate.

$^1$H NMR (MeOD, 400 MHz): 1.79-1.89 (m, 2H, —CH—C$\underline{H}_2$), 1.97-2.12 (m, 2H, —CH—C$\underline{H}_2$), 2.30-2.40 (m, 1H, —O—CH—C$\underline{H}$), 3.18-3.30 (m, 6H, N—C$\underline{H}_2$—CH$_2$, N—C$\underline{H}_2$—CH$_2$, N—C$\underline{H}_2$—CH$_2$), 3.59-3.75 (m, 1H, —O—CH—CH$_2$)

Elementary analysis of $C_{14}H_{12}F_5NO_3$
Theoretical value: C, 49.8; H, 3.6; N, 4.1
Experimental value: C, 49.1; H, 4.4; N, 3.8

Example 2

Preparation of Solifenacin Intermediate 127.2 g (1.0 mol) of (R)-quinuclidinol was dissolved in 1270 mL of dichloromethane and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, 1270 mL of water was added to the reaction solution, and then the pH of the reaction solution was adjusted to 9~10 using ammonium hydroxide. Then, an organic layer was separated from the reaction solution. Finally, the reaction solution was washed with 1270 mL of water, dried with $MgSO_4$ and then concentrated under reduced pressure to obtain 300.8 g (89.2%) of (3R)-1-azabicyclo[2,2,2]oct-3-yl pentafluorophenylcarbonate.

Here, elementary analysis and spectral data are the same as those of Example 1.

Example 3

Preparation of Solifenacin Intermediate 127.2 g (1.0 mol) of (R)-quinuclidinol was dissolved in 1270 mL of ethyl acetate and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, 1270 mL of water was added to the reaction solution, and then the pH of the reaction solution was adjusted to 9~10 using ammonium hydroxide. Then, an organic layer was separated from the reaction solution. Finally, the reaction solution was washed with 1270 mL of water, dried with $MgSO_4$ and then concentrated under reduced pressure to obtain 298.1 g (88.4%) of (3R)-1-azabicyclo[2,2,2]oct-3-yl pentafluorophenylcarbonate.

Here, elementary analysis and spectral data are the same as those of Example 1.

Example 4

Preparation of Solifenacin Intermediate 127.2 g (1.0 mol) of (R)-quinuclidinol was dissolved in 1270 mL of isopropanol and then stirred at 10~15° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 10~15° C. for 10~12 hours. After confirming the completion of a reaction using thin layer chromatography (TLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, 1270 mL of water was added to the reaction solution, and then the pH of the reaction solution was adjusted to 9~10 using ammonium hydroxide. Then, an organic layer was separated from the reaction solution. Finally, the reaction solution was washed with 1270 mL of water, dried with $MgSO_4$ and then concentrated under reduced pressure to obtain 295.4 g (87.6%) of (3R)-1-azabicyclo[2,2,2]oct-3-yl pentafluorophenylcarbonate.

Here, elementary analysis and spectral data are the same as those of Example 1.

Example 5

Preparation of solifenacin 337.2 g (1.0 mol) of the (3R)-1-azabicyclo[2,2,2]oct-3-yl pentafluorophenylcarbonate prepared in Example 1 was dissolved in 337 mL of toluene to obtain a reaction solution. Subsequently, 209.3 g (1.0 mol) of (1S)-1-phenyl-1,2,3,4-tetrahydroisoquinoline was added to the reaction solution, and then stirred at 10~15° C. for 9~10 hours. After confirming the completion of a reaction using high performance liquid chromatography (HPLC), the reaction solution was concentrated under reduced pressure. Subsequently, 1400 mL water was added to the reaction solution, and concentrated hydrochloric acid was added dropwise into the reaction solution to adjust the pH of the reaction solution to 1~2. Then, the reaction solution was washed with 1400 mL of toluene to remove pentafluorophenol (a by-product formed during the reaction) from the reaction product. Then, an aqueous layer was extracted from the reaction solution using 1400 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Then, an organic layer was separated from the reaction solution. Finally, the reaction solution was washed with 1400 mL of water, dried with $MgSO_4$ and then concentrated under reduced pressure to obtain 329.8 g (91.0%) of solifenacin.

$^1$H NMR (MeOD, 400 MHz): 1.89-2.21 (m, 4H, —CH—C$\underline{H}_2$, —CH—C$\underline{H}_2$), 2.34 (m, 1H, —CH—C$\underline{H}$—CH$_2$), 2.75-3.10 (m, 3H, —N—CH$_2$—C$\underline{H}_2$—CH, —N—CH$_2$—C$\underline{H}_2$—CH), 3.17-3.40 (m, 5H, —N—CH$_2$—C$\underline{H}_2$—CH, —N—C$\underline{\vec{H}_2}$—CH$_2$, —N—C$\underline{H}_2$—CH$_2$), 3.60-3.63 (m, 2H, —N—C$\underline{H}_2$—CH$_2$—CH), 3.93 (m, 1H, —N—C$\underline{H}_2$—CH$_2$—CH), 5.03 (m, 1H, —O—C$\underline{H}$—CH), 6.22-6.35 (m, 1H, —N—C$\underline{H}$—CH), 7.08-7.28 (m, 9H, aromatic H)

Example 6

Preparation of Solifenacin 337.2 g (1.0 mol) of the (3R)-1-azabicyclo[2,2,2]oct-3-yl pentafluorophenylcarbonate prepared in Example 2 was dissolved in 337 mL of toluene to obtain a reaction solution. Subsequently, 209.3 g (1.0 mol) of (1S)-1-phenyl-1,2,3,4-tetrahydroisoquinoline was added to the reaction solution, and then stirred at 25~30° C. for 4~5 hours. After confirming the completion of a reaction using high performance liquid chromatography (HPLC), the reaction solution was concentrated under reduced pressure. Subsequently, 1400 mL water was added to the reaction solution, and concentrated hydrochloric acid was added dropwise into the reaction solution to adjust the pH of the reaction solution to 1~2. Then, the reaction solution was washed with 1400 mL of toluene to remove pentafluorophenol (a by-product formed during the reaction) from the reaction product. Then, an aqueous layer was extracted from the reaction solution using 1400 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Then, an organic layer was separated from the reaction solution. Finally, the reaction solution was washed with 1400 mL of water, dried with $MgSO_4$ and then concentrated under reduced pressure to obtain 320.4 g (88.4%) of solifenacin.

Here, spectral data are the same as those of Example 5.

Example 7

Preparation of Solifenacin 337.2 g (1.0 mol) of the (3R)-1-azabicyclo[2,2,2]oct-3-yl pentafluorophenylcarbonate prepared in Example 1 was dissolved in 337 mL of dichloromethane to obtain a reaction solution. Subsequently, 209.3 g (1.0 mol) of (1S)-1-phenyl-1,2,3,4-tetrahydroisoquinoline was added to the reaction solution, and then stirred at 25~30° C. for 4~5 hours. After confirming the completion of a reaction using high performance liquid chromatography (HPLC), the reaction solution was concentrated under reduced pressure. Subsequently, 1400 mL water was added to the reaction solution, and concentrated hydrochloric acid was added dropwise into the reaction solution to adjust the pH of the reaction solution to 1~2. Then, the reaction solution was washed with 1400 mL of toluene to remove pentafluorophenol (a by-product formed during the reaction) from the reaction product. Then, an aqueous layer was extracted from the reaction solution using 1400 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Then, an organic layer was separated from the reaction solution. Finally, the reaction solution was washed with 1400 mL of water, dried with $MgSO_4$ and then concentrated under reduced pressure to obtain 318.2 g (87.8%) of solifenacin.

Here, spectral data are the same as those of Example 5.

Example 8

Preparation of Solifenacin 337.2 g (1.0 mol) of the (3R)-1-azabicyclo[2,2,2]oct-3-yl pentafluorophenylcarbonate prepared in Example 1 was dissolved in 337 mL of acetone to obtain a reaction solution. Subsequently, 209.3 g (1.0 mol) of (1S)-1-phenyl-1,2,3,4-tetrahydroisoquinoline was added to the reaction solution, and then stirred at 25~30° C. for 4~5 hours. After confirming the completion of a reaction using high performance liquid chromatography (HPLC), the reaction solution was concentrated under reduced pressure. Subsequently, 1400 mL water was added to the reaction solution, and concentrated hydrochloric acid was added dropwise into the reaction solution to adjust the pH of the reaction solution to 1~2. Then, the reaction solution was washed with 1400 mL of toluene to remove pentafluorophenol (a by-product formed during the reaction) from the reaction product. Then, an aqueous layer was extracted from the reaction solution using 1400 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Then, an organic layer was separated from the reaction solution. Finally, the reaction solution was washed with 1400 mL of water, dried with $MgSO_4$ and then concentrated under reduced pressure to obtain 320.4 g (88.4%) of solifenacin.

Here, spectral data are the same as those of Example 5.

Example 9

Preparation of Solifenacin 337.2 g (1.0 mol) of the (3R)-1-azabicyclo[2,2,2]oct-3-yl pentafluorophenylcarbonate prepared in Example 1 was dissolved in 337 mL of isopropanol to obtain a reaction solution. Subsequently, 209.3 g (1.0 mol) of (1S)-1-phenyl-1,2,3,4-tetrahydroisoquinoline was added to the reaction solution, and then stirred at 10~15° C. for 9~11 hours. After confirming the completion of a reaction using high performance liquid chromatography (HPLC), the reaction solution was concentrated under reduced pressure. Subsequently, 1400 mL water was added to the reaction solution, and concentrated hydrochloric acid was added dropwise into the reaction solution to adjust the pH of the reaction solution to 1~2. Then, the reaction solution was washed with 1400 mL of toluene to remove pentafluorophenol (a by-product formed during the reaction) from the reaction product. Then, an aqueous layer was extracted from the reaction solution using 1400 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Then, an organic layer was separated from the reaction solution. Finally, the reaction solution was washed with 1400 mL of water, dried with $MgSO_4$ and then concentrated under reduced pressure to obtain 326.9 g (90.2%) of solifenacin.

Here, spectral data are the same as those of Example 5.

Example 10

Preparation of Solifenacin 337.2 g (1.0 mol) of the (3R)-1-azabicyclo[2,2,2]oct-3-yl pentafluorophenylcarbonate prepared in Example 1 was dissolved in 337 mL of ethyl acetate to obtain a reaction solution. Subsequently, 209.3 g (1.0 mol) of (1S)-1-phenyl-1,2,3,4-tetrahydroisoquinoline was added to the reaction solution, and then stirred at 25~30° C. for 4~5 hours. After confirming the completion of a reaction using high performance liquid chromatography (HPLC), the reaction solution was concentrated under reduced pressure. Subsequently, 1400 mL water was added to the reaction solution, and concentrated hydrochloric acid was added dropwise into the reaction solution to adjust the pH of the reaction solution to 1~2. Then, the reaction solution was washed with 1400 mL of toluene to remove pentafluorophenol (a by-product formed during the reaction) from the reaction product. Then, an aqueous layer was extracted from the reaction solution using 1400 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Then, an organic layer was separated from the reaction solution. Finally, the reaction solution was washed with 1400 mL of water, dried with $MgSO_4$ and then concentrated under reduced pressure to obtain 220.4 g (88.4%) of solifenacin.

Here, spectral data are the same as those of Example 5

Example 11

Preparation of Solifenacin Succinate 127.2 g (1.0 mol) of (R)-quinuclidinol was dissolved in 1270 mL of toluene and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), 209.3 g (1.0 mol) of (1S)-1-phenyl-1,2,3,4-tetrahydroisoquinoline was added to the reaction solution, and then stirred at 25~30° C. for 4~5 hours. After confirming the completion of a reaction using high performance liquid chromatography (HPLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Subsequently, 1270 mL of acetone and 118.1 g (1.0 mol) of succinic acid were added to the reaction solution, stirred at 55~60° C. for 30 minutes, further stirred at 10~15° C. for 2 hours, and then filtered to obtain a reaction product. Finally, the reaction product was washed with 640 mL of toluene and 640 mL of acetone, and then dried in vacuum at 40° C. to obtain 390.2 g (81.2%) of solifenacin succinate.

HPLC content: 99.9%, optical purity: 99.95%
Melting point: 146~148° C.
$^1$H NMR (MeOD, 400 MHz): 1.89-2.21 (m, 4H, —CH—C$\underline{H}_2$, —CH—C$\underline{H}_2$), 2.34 (m, 1H, —CH—C$\underline{H}$—CH$_2$), 2.49 (s, 4H, —O—CO—C$\underline{H}_2$—C$\underline{H}_2$—), 2.75-3.10 (m, 3H, —N—CH$_2$—C$\underline{H}_2$—CH, —N—CH$_2$—C$\underline{H}_2$—CH), 3.17-3.40 (m, 5H, —N—CH$_2$—C$\underline{H}_2$—CH, —N—C$\underline{H}_2$—CH$_2$, —N—C$\underline{H}_2$—CH$_2$), 3.60-3.63 (m, 2H, —N—C$\underline{H}_2$—CH$_2$—CH), 3.93 (m, 1H, —N—C$\underline{H}_2$—CH$_2$—CH), 5.03 (m, 1H, —O—C$\underline{H}$—CH), 6.22-6.35 (m, 1H, —N—CH—CH), 7.08-7.28 (m, 9H, aromatic H)

Elementary analysis of $C_{27}H_{32}N_2O_6$
Theoretical value: C, 67.4; H, 6.7; N, 5.8
Experimental value: C, 66.7; H, 6.7; N, 5.8

Example 12

Preparation of Solifenacin Succinate 127.2 g (1.0 mol) of (R)-quinuclidinol was dissolved in 1270 mL of dichloromethane and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), 209.3 g (1.0 mol) of (1S)-1-phenyl-1,2,3,4-tetrahydroisoquinoline was added to the reaction solution, and then stirred at 25~30° C. for 4~5 hours. After confirming the completion of a reaction using high performance liquid chromatography (HPLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Subsequently, 1270 mL of acetone and 118.1 g (1.0 mol) of succinic acid were added to the reaction solution, stirred at 55~60° C. for 30 minutes, further stirred at 10~15° C. for 2 hours, and then filtered to obtain a reaction product. Finally, the reaction product was washed with 640 mL of toluene and 640 mL of acetone, and then dried in vacuum at 40° C. to obtain 381.5 g (79.4%) of solifenacin succinate.

HPLC content: 99.9%,
Optical purity: 99.95%
Here, melting point, elementary analysis and spectral data are the same as those of Example 11.

Example 13

Preparation of Solifenacin Succinate 127.2 g (1.0 mol) of (R)-quinuclidinol was dissolved in 1270 mL of dichloromethane and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), the reaction solution was concentrated under reduced pressure.

Subsequently, oily matter obtained by adding 1270 mL of acetone to the reaction solution was dissolved, and then 209.3 g (1.0 mol) of (1S)-1-phenyl-1,2,3,4-tetrahydroisoquinoline was added to the reaction solution and stirred at 25~30° C. for 4~5 hours. After confirming the completion of a reaction using high performance liquid chromatography (HPLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Subsequently, 1270 mL of acetone and 118.1 g (1.0 mol) of succinic acid were added to the reaction solution, stirred at 55~60° C. for 30 minutes, further stirred at 10~15° C. for 2 hours, and then filtered to obtain a reaction product. Finally, the reaction product was washed with 640 mL of toluene and 640 mL of acetone, and then dried in vacuum at 40° C. to obtain 377.2 g (78.5%) of solifenacin succinate.

HPLC content: 99.9%,
Optical purity: 99.95%
Here, melting point, elementary analysis and spectral data are the same as those of Example 11.

Example 14

Preparation of Solifenacin Succinate 127.2 g (1.0 mol) of (R)-quinuclidinol was dissolved in 1270 mL of dichloromethane and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), the reaction solution was concentrated under reduced pressure. Subsequently, oily matter obtained by adding 1270 mL of isopropanol to the reaction solution was dissolved, and then 209.3 g (1.0 mol) of (1S)-1-phenyl-1,2,3,4-tetrahydroisoquinoline was added to the reaction solution and stirred at 25~30° C. for 4~5 hours. After confirming the completion of a reaction using high performance liquid chromatography (HPLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Subsequently, 1270 mL of acetone and 118.1 g (1.0 mol) of succinic acid were added to the reaction solution, stirred at 55~60° C. for 30 minutes, further stirred at 10~15° C. for 2 hours, and then filtered to obtain a reaction product. Finally, the reaction product was washed with 640 mL of toluene and 640 mL of acetone, and then dried in vacuum at 40° C. to obtain 386.4 g (80.4%) of solifenacin succinate.

HPLC content: 99.9%,

Optical purity: 99.95%

Here, melting point, elementary analysis and spectral data are the same as those of Example 11.

Example 15

Preparation of Solifenacin Succinate 127.2 g (1.0 mol) of (R)-quinuclidinol was dissolved in 1270 mL of dichloromethane and then stirred at 25~30° C. for 20 minutes to obtain a reaction solution. Subsequently, 472.9 g (1.2 mol) of bis(pentafluorophenyl)carbonate was added to the reaction solution to form a suspended reaction solution, and then the suspended reaction solution was stirred at 25~30° C. for 3~4 hours. After confirming the completion of a reaction using thin layer chromatography (TLC), the reaction solution was concentrated under reduced pressure. Subsequently, oily matter obtained by adding 1270 mL of ethyl acetate to the reaction solution was dissolved, and then 209.3 g (1.0 mol) of (1S)-1-phenyl-1,2,3,4-tetrahydroisoquinoline was added to the reaction solution and stirred at 25~30° C. for 4~5 hours. After confirming the completion of a reaction using high performance liquid chromatography (HPLC), the reaction solution was concentrated under reduced pressure. Subsequently, 1270 mL water was added to the reaction solution, and concentrated hydrochloric acid was added dropwise into the reaction solution to adjust the pH of the reaction solution to 1~2. Then, the reaction solution was washed with 1270 mL of toluene to remove pentafluorophenol (a by-product formed during the reaction) from the reaction product. Then, an aqueous layer was extracted from the reaction solution using 1270 mL of dichloromethane, and then the reaction solution was concentrated under reduced pressure. Then, 1270 mL of water was added to the reaction solution, the pH of the reaction solution was adjusted to 9~10 using ammonium hydroxide, and then an aqueous layer was further extracted from the reaction solution using 1270 mL of toluene. Subsequently, 1270 mL of acetone and 118.1 g (1.0 mol) of succinic acid were added to the reaction solution, stirred at 55~60° C. for 30 minutes, further stirred at 10~15° C. for 2 hours, and then filtered to obtain a reaction product. Finally, the reaction product was washed with 640 mL of toluene and 640 mL of acetone, and then dried in vacuum at 40° C. to obtain 384.9 g (80.1%) of solifenacin succinate.

HPLC content: 99.9%,

Optical purity: 99.95%

Here, melting point, elementary analysis and spectral data are the same as those of Example 11.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing solifenacin or a salt thereof, comprising the steps of:

(a) reacting (R)-quinuclidinol of Formula (VI):

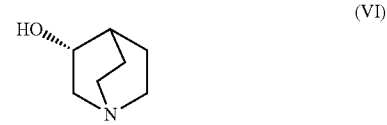

with bis(pentafluorophenyl)carbonate of Formula (VII):

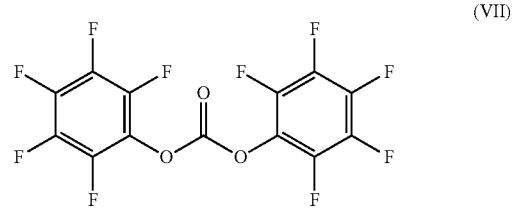 [SMILES: O=C(Oc1c(F)c(F)c(F)c(F)c1F)Oc1c(F)c(F)c(F)c(F)c1F]

in an organic solvent to prepare (3R)-1-azabicyclo[2,2,2]oct-3-yl pentafluorophenylcarbonate of Formula (IV):

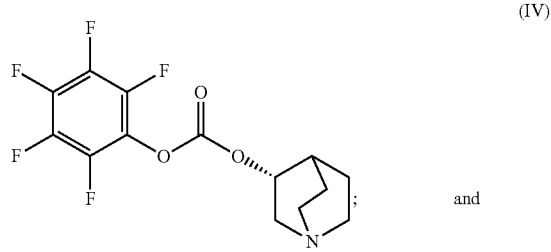 [SMILES: O=C(Oc1c(F)c(F)c(F)c(F)c1F)O[C@H]1CN2CCC1CC2]

and (b) reacting the (3R)-1-azabicyclo[2,2,2]oct-3-yl pentafluorophenylcarbonate of Formula (IV):

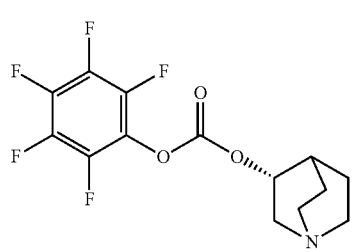

with (1S)-1-phenyl-1,2,3,4-tetrahydroisoquinoline of Formula (V):

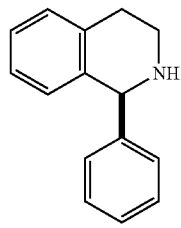

in an organic solvent to prepare solifenacin of Formula (II):

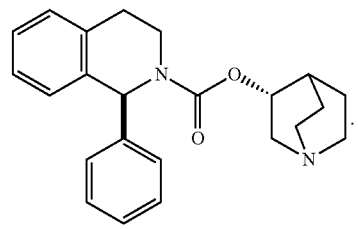

2. The method of claim 1, further comprising the step of converting the solifenacin of Formula (II):

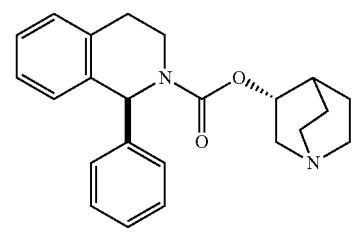

into solifenacin succinate of Formula (I):

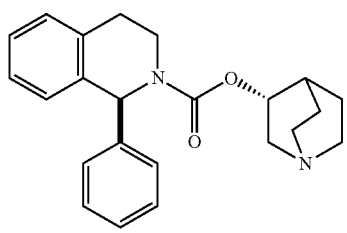

3. The method of claim 1, wherein, in the step (a), an amount of 1 to 3 molar equivalents of bis(pentafluorophenyl) carbonate of Formula (VII) per 1 molar equivalent of (R)-quinuclidinol of Formula (VI) is used.

4. The method of claim 1, wherein, in the step (a) or (b), the reaction is performed at a temperature of 10° C. to 30° C.

5. The method of claim 4, wherein, in the step (a) or (b), the reaction is performed for 2 hours to 12 hours.

6. The method of claim 1, wherein, in the step (a) or (b), the reaction is performed without using a base.

7. The method of claim 1, wherein, in the step (a) or (b), the organic solvent is selected from the group consisting of toluene, ethyl acetate, dichloromethane, acetone, isopropanol and mixtures thereof.

8. The method of claim 1, wherein the step (b) is performed by an in-situ reaction in which the (1S)-1-phenyl-1,2,3,4-tetrahydroisoquinoline of Formula (V) is added dropwise without dissociating the (3R)-1-azabicyclo[2,2,2]oct-3-yl pentafluorophenylcarbonate of Formula (IV) prepared in the step (a).

9. The method of claim 2, wherein the step (c) is performed in the presence of an organic solvent selected from the group consisting of aliphatic alcohol, ketone, ester, aromatic hydrocarbon, polar aliphatic hydrocarbon and mixtures thereof.

10. The method of claim 9, wherein, in the step (c), the organic solvent is toluene, acetone or a mixture thereof.

11. A compound represented by Formula (IV):
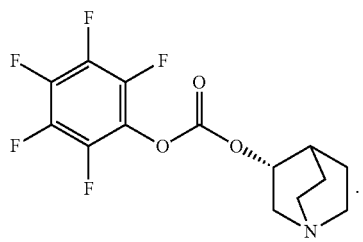
(IV)
12. A method of preparing a compound of Formula (IV):
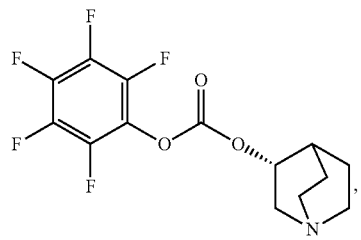
(IV)
comprising the step of reacting (R)-quinuclidinol of Formula (VI):
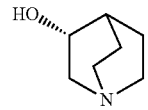
(VI)
with bis(pentafluorophenyl)carbonate of Formula (VII):
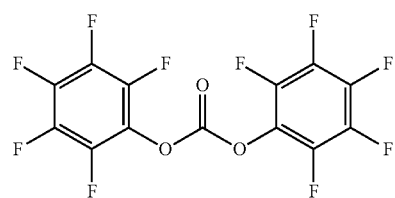
(VII)
in an organic solvent.
* * * * *